US009795448B2

(12) United States Patent
Hong et al.

(10) Patent No.: US 9,795,448 B2
(45) Date of Patent: Oct. 24, 2017

(54) SURGERY ROBOT (71) Applicant: Daegu Gyeongbuk Institute of Science & Technology, Daegu (KR)

(72) Inventors: Jae Sung Hong, Daegu (KR); Byung Sik Cheon, Daeju (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 141 days.

(21) Appl. No.: 14/427,599

(22) PCT Filed: Jun. 21, 2013

(86) PCT No.: PCT/KR2013/005476
§ 371 (c)(1),
(2) Date: Mar. 11, 2015

(87) PCT Pub. No.: WO2014/042339
PCT Pub. Date: Mar. 20, 2014

(65) Prior Publication Data
US 2015/0245873 A1 Sep. 3, 2015

(30) Foreign Application Priority Data
Sep. 14, 2012 (KR) .................. 10-2012-0101898

(51) Int. Cl.
*A61B 17/00* (2006.01)
*A61B 19/00* (2006.01)
(Continued)

(52) U.S. Cl.
CPC .... *A61B 19/2203* (2013.01); *A61B 17/00234* (2013.01); *A61B 34/30* (2016.02);
(Continued)

(58) Field of Classification Search
CPC ............ A61B 1/0087; A61B 17/00234; A61B 2017/00318; A61B 34/30; A61B 2034/301; A61B 2034/305; A61B 2217/005
See application file for complete search history.

(56) References Cited

U.S. PATENT DOCUMENTS 5,611,813 A * 3/1997 Lichtman ............... A61B 17/29
606/174
6,394,998 B1 * 5/2002 Wallace ................. A61B 34/71
606/1
(Continued)

FOREIGN PATENT DOCUMENTS

| JP | 2008100323 A | 5/2008 |
| JP | 2008105116 A | 5/2008 |
| KR | 101146482 B1 | 5/2012 |

OTHER PUBLICATIONS

Cheon, et al., "Design of a New Single Port Surgery Robot with Large Torque and Workspace," 16:20-16-40, IAS-12, The 12th International Conf. on Intelligent Autonomous-Systems, Jun. 26-29, 2012.
(Continued)

*Primary Examiner* — Tammie K Heller
(74) *Attorney, Agent, or Firm* — Eversheds Sutherland (US) LLP (57) ABSTRACT A surgery robot according to one embodiment of the present invention includes: a position transformation unit having at least one portion which can be introduced into the body, wherein the position transformation unit is formed into a plurality of joints so as to be capable of positional transformation; a surgery unit which is coupled to the position transformation unit and the position of which is transformed along with the position transformation of the position transformation unit, wherein a surgery section is mounted on one portion of the distal end thereof for performing surgery on an affected area; and a driving unit which generates a driving force for the positional transformation of the position trans-
(Continued)

formation unit, wherein the driving unit may have a driving section and a driving transmission section which adjusts the position of one of the joints with respect to another of the joints.

11 Claims, 5 Drawing Sheets

(51) Int. Cl.
    *A61B 34/30*        (2016.01)
    *A61B 90/00*        (2016.01)

(52) U.S. Cl.
    CPC ....... *A61B 90/361* (2016.02); *A61B 2034/305* (2016.02); *A61B 2217/005* (2013.01); *Y10S 901/19* (2013.01)

(56) References Cited

U.S. PATENT DOCUMENTS

| | | | |
|---|---|---|---|
| 2003/0036748 A1 | 2/2003 | Cooper et al. | |
| 2005/0033270 A1 | 2/2005 | Ramans et al. | |
| 2009/0171374 A1* | 7/2009 | Omori | A61B 34/71 606/130 |

OTHER PUBLICATIONS

Abstract—Korea Society of Medical Robot—2012.
Chun, et al., "Development of Single Port Surgery Robot Having Great Torque and Wide Working Area," The 7th Korea Robotics Society Annual Conference—Digest Book 2012-21-23.

* cited by examiner

FIG. 5

SURGERY ROBOT

TECHNICAL FIELD

The present invention relates to a surgery robot, and more particularly, to a surgery robot that employs a driving transmission section of a plate spring type for adjusting a position of a surgery unit performing surgery on an affected part to generate a high torque, thereby securing a sufficient force required for the surgery.

BACKGROUND ART

In general, a laparoscopic surgery robot is a robot performing minimally invasive surgery (MIS) using a laparoscope and small surgical instruments. Here, MIS refers to a surgical technique of abdominally introducing instruments into the body through three or four small incisions to accurately and safely perform surgery, for example, cholecystectomy, prostatic surgery, gastrotomy, and tumor excision.

When compared to general surgical operations, patients undergoing such an MIS have reduced pain and a short recovery period after the surgery and thus, may return to normal lives within a short period of time. Such advantages are giving rise to an increased demand for various robots and surgical instruments for performing the MIS and accordingly, development of various robots and instruments is progressing.

Conventional surgical robots generally include a robotic arm in a multi joint structure, wherein the robotic arm includes a surgery unit for surgery at a front end portion thereof, a suction unit to remove materials from a surgical site and an image capturing unit to capture a real-time video of an internal state.

In the conventional surgical robots, a wire is used to operate the surgery unit of the robot arm. However, when a driving force is transmitted through the wire, a sufficient force to hold and move an organ in the body may not be secured and a surgical area may be limited.

Therefore, developing a surgical robot which generates high torque and secures a wide area for surgery to smoothly perform surgery is required.

DISCLOSURE OF INVENTION

Technical Goals

An aspect of the present invention is to provide a surgery robot in which positions of joints of a position change unit for adjusting a position of a surgery unit are adjusted not by a wire but by a driving transmission section of a plate spring (or leaf spring) type which is capable of providing high torque, thereby ensuring sufficient force for surgery and securing a wide area for surgery.

Another aspect of the present invention is to provide a surgery robot in which accurate driving transmission is achieved by a driving transmission section to improve accuracy of a surgical procedure, and equipment may be installed at reduced cost, so that high cost may not be imposed on patients, thus lightening burden of the patients.

Technical Solutions

According to an aspect of the present invention, there is provided a surgery robot including a position change unit including at least one portion introduced into a body and including a plurality of joints to change a position, a surgery unit coupled to the position change unit of which a position is to be changed along with a position change of the position change unit, including a surgery section for performing surgery on an affected area mounted on a front end portion thereof, and a driving unit to generate a driving force for the position change of the position change unit, wherein the driving unit includes a driving section to generate the driving force, and a driving transmission section which is disposed along one surface of the joints and a degree of unfolding or bending is adjusted by the driving force provided from the driving section to control a position of one joint with respect to another joint. With this configuration, positions of the joints of the position change unit for adjusting a position of the surgery unit are adjusted not by a wire but by the driving transmission section of a plate spring type which is capable of providing high torque, thereby ensuring sufficient force for surgery and securing a wide area for surgery.

The driving transmission section may be provided as a plate spring (or leaf spring) type so as to change positions of the joints depending on the degree of unfolding or bending.

The plurality of joints of the position change unit may include a first joint in a lengthwise direction, a second joint coupled to the first joint in a tilting manner, and a third joint coupled to the second joint in a tilting manner, the third joint tilting in a direction crossing a direction of the second joint with respect to the first joint, and the driving transmission section may be disposed along one surface of the first joint and one surface of the second joint and one end portion is fixed to the second joint.

A guide member to lead a movement of the driving transmission section may be provided on one surface of at least one of the joints.

The surgery unit may further include a connection section having flexibility to be partly fixed to the position change unit and coupled to the surgery section at an end portion thereof, and the surgery section may be capable of tilting at the same spot with respect to the connection section.

The position change unit may include at least one coupling ring in a ring shape to which the connection section is coupled by passing therethrough to detachably couple the surgery unit to the position change unit.

The surgery robot may further include a suction unit coupled to the position change unit to remover a material generated at a surgical site during surgery by the surgery unit. The surgery robot may further include an image capture unit coupled to the position change unit to capture a video of a surgical procedure or position of the surgery section in real time during surgery by the surgery unit.

According to an aspect of the present invention, there is provided a surgery robot including a surgery unit having at least one portion introduced into a body and including a plurality of joints to change a position and a surgery section at a front end portion thereof, a driving unit to generate a driving force for changing a position of the surgery unit, and a driving transmission unit disposed along the plurality of joints and unfolded or bent by the driving force from the driving unit to change the position of the surgery unit, and accordingly high torque may be provided to ensure sufficient force for surgery and a wide area for surgery may be secured.

The plurality of joints may include a first joint, and a second joint coupled to the first joint in a hinged manner, and the driving transmission unit may be disposed along one side of the first joint and one side of the second joint and one end fixed to the second joint.

Effects of Invention

As described above, according to an embodiment, positions of joints of a position change unit for adjusting a position of a surgery unit are adjusted not by a wire but by a driving transmission section of a plate spring type which is capable of providing high torque, thereby ensuring sufficient force for surgery and securing a wide area for surgery.

According to another embodiment of the present invention, accurate driving transmission is achieved by a driving transmission section to improve accuracy of a surgical procedure, and equipment may be installed at reduced cost, so that high cost may not be imposed on patients, thus lightening burden of the patients.

BEST MODE FOR CARRYING OUT INVENTION

Reference will now be made in detail to example embodiments of the present invention, examples of which are illustrated in the accompanying drawings, wherein like reference numerals refer to the like elements throughout. The embodiments are described below in order to explain the present invention by referring to the figures. The following description is one of diverse aspects of the present invention which can be claimed for a patent and constitutes part of the detailed description of the present invention.

In describing the present invention, detailed descriptions related to a known function or configuration will be omitted herein so as to clarify the substance of the present invention.

Figure 1:
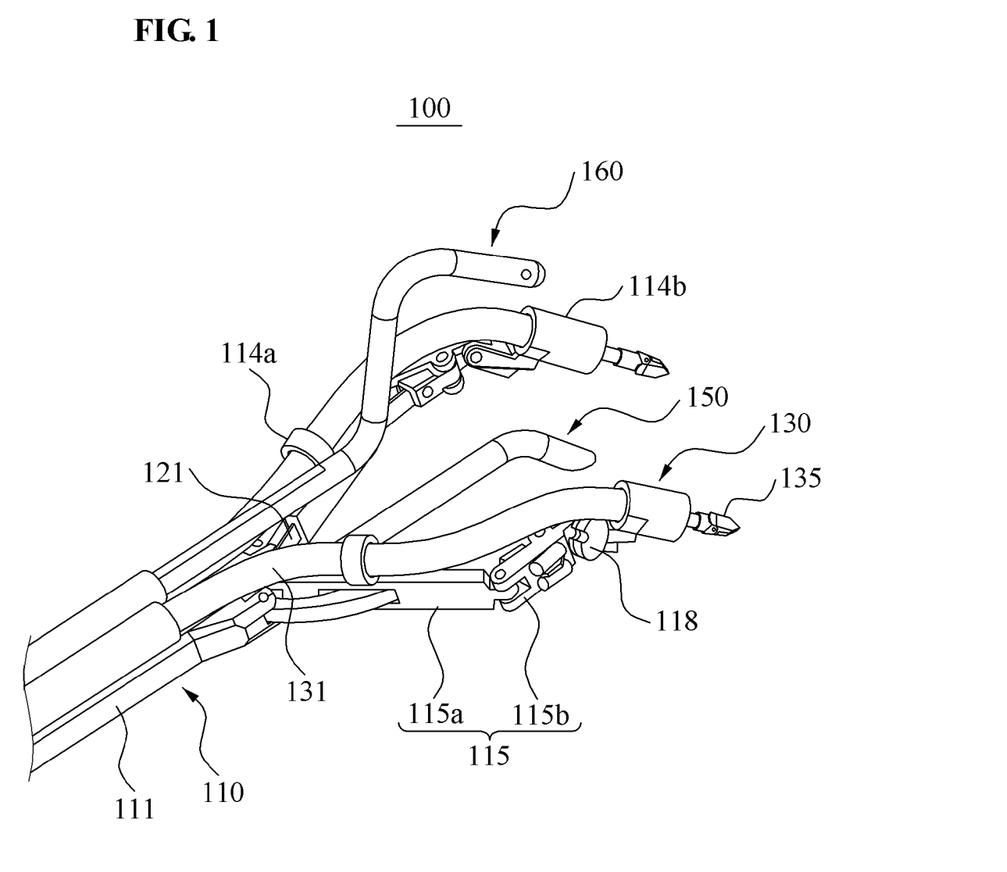
FIG. 1 is a perspective view of a surgery robot according to an embodiment of the present invention.
Figure 2:
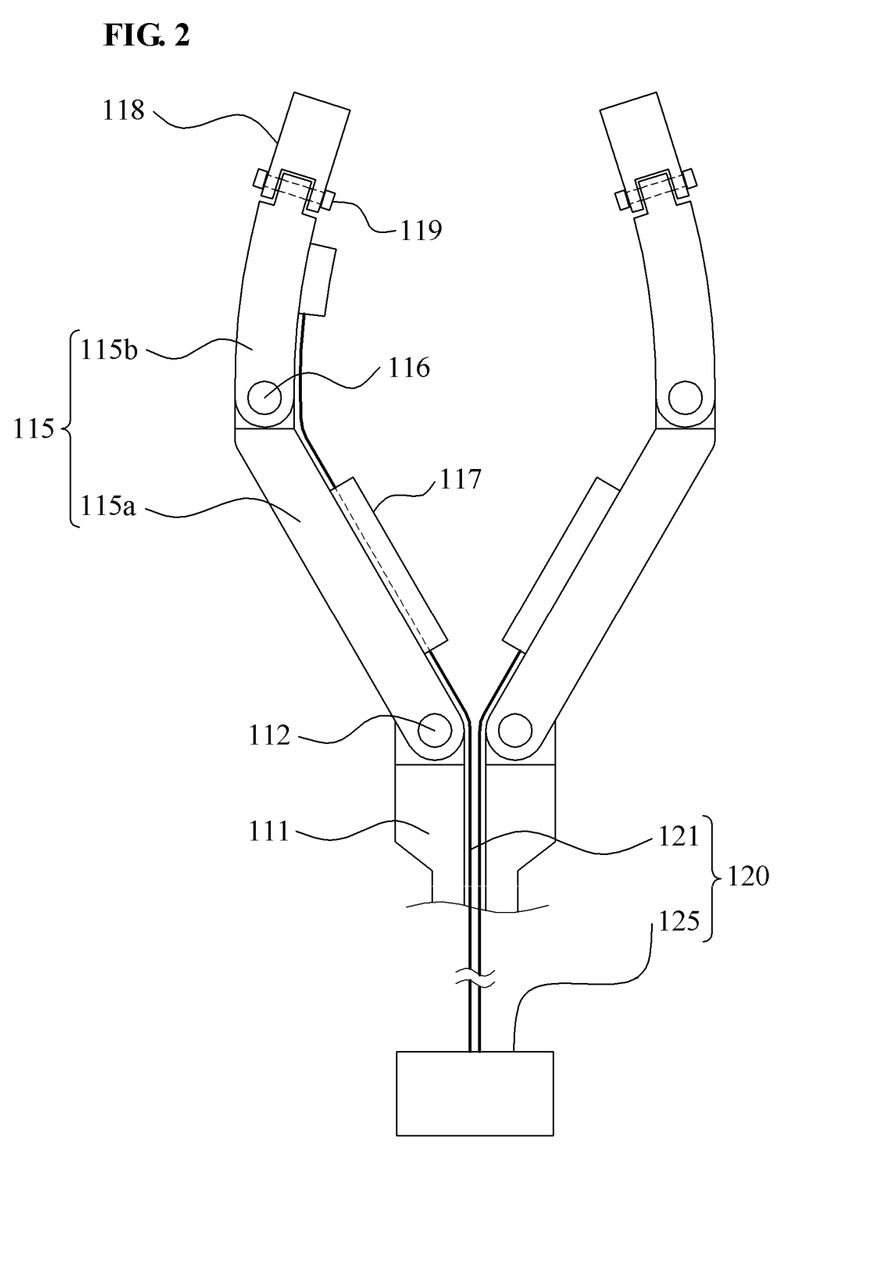
FIG. 2 schematically illustrates a position change unit in FIG. 1.
Figure 3:
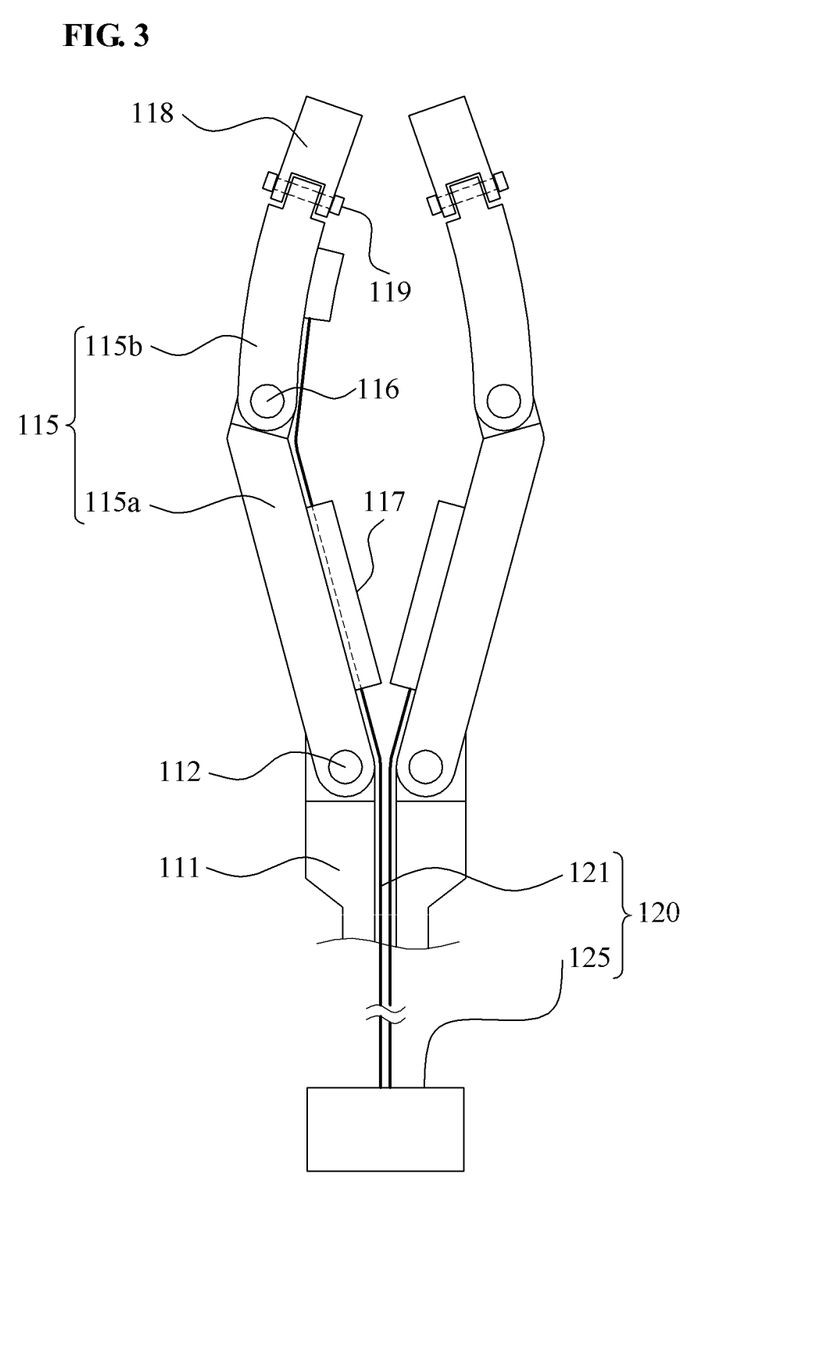
FIG. 3 schematically illustrates a state of the position change unit changing a position based on an operation of a driving transmission section in FIG. 2.
Figure 4:
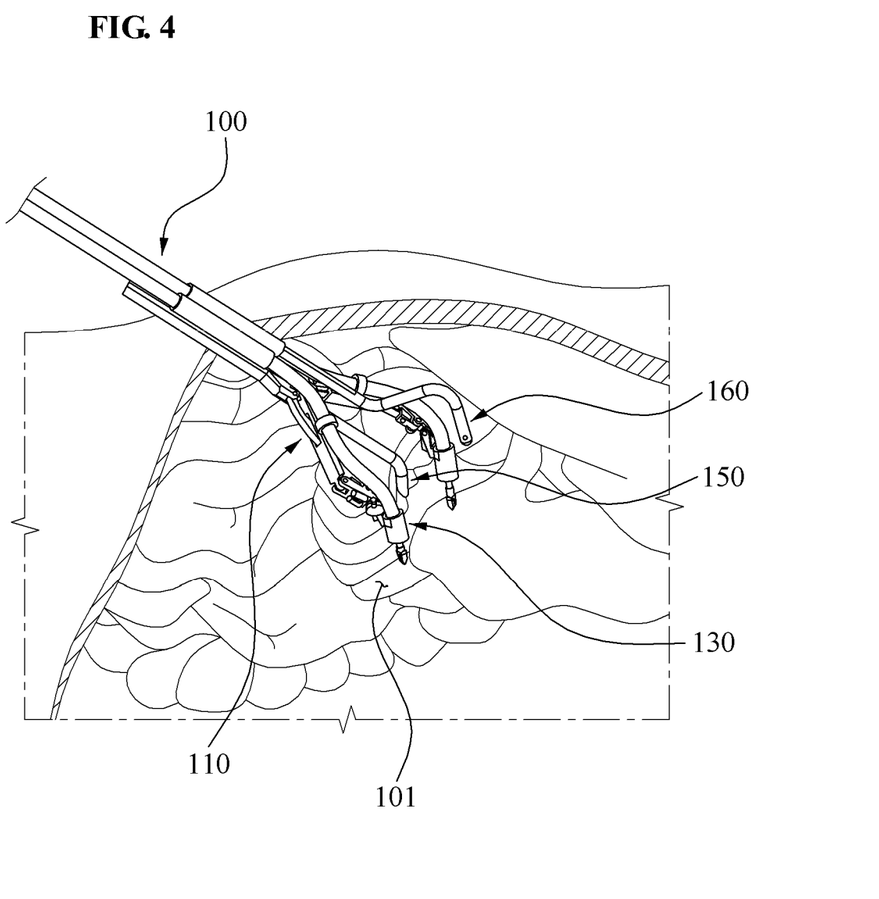
FIG. 4 illustrates an application of the surgery robot of FIG. 1.

FIG. 1 is a perspective view of a surgery robot according to an embodiment of the present invention, FIG. 2 schematically illustrates a position change unit in FIG. 1, FIG. 3 schematically illustrates a state of the position change unit changing a position based on an operation of a driving transmission section in FIG. 2, and FIG. 4 illustrates an application of the surgery robot of FIG. 1.

Referring to FIGS. 1 to 3, the surgery robot 100 according to the embodiment of the present invention is for laparoscopic surgery and may include the position change unit 110 which is introduced into a body and includes a plurality of joints 111, 115 and 118 for changing a position based on external control instructions, for example, an operation by a surgeon, a surgery unit 130 which is coupled to the position change unit 110 to be changed in position along with a position change of the position change unit 110 and includes a surgery section 135 mounted on a front end portion thereof, and a driving unit 120 to generate a driving force for a position change of the position change unit 110.

Here, the driving unit 120, which will be described in detail, may include a driving section 125 for generating a driving force and a driving transmission section 121 disposed among the plurality of joints 111, 115 and 118 to adjust relative positions of the joints depending on the driving force from the driving section 125. The driving transmission section 125 is provided in a form of a plate spring (or leaf spring) type which ensures transmission of the driving force to obtain high torque, thus securing a wide area for surgery as compared with a conventional art, which will be described in detail.

Describing each component, the position change unit 110, which forms a basic frame of the surgery robot 100, may include the plurality of joints 111, 115 and 118. The position change unit 110 has a structure that the plurality of joints 111, 115 and 118 is spreaded (spreading straight), when the position change unit 110 is introduced into the body, and is unfolded in the body after the position change unit 110 is introduced. Thus, part of the surgery robot 100 of the present embodiment may be smoothly introduced into the body through small incisions made on the body.

The plurality of joints 111, 115 and 118 may be connected and coupled to each other in a hinged manner, and accordingly have a tilting structure. In detail, the joints 111, 115 and 118 forming the position change unit 110 of the present embodiment may include, as illustrated in FIG. 1, first joints 111 in a lengthwise direction, second joints 115 coupled to the first joints 111 in a tilting manner, and third joints 118 coupled to the second joints 115 in a tilting manner.

The first joints 111, which are basic joints of the position change unit 110, not only serve as a base for other joints 115 and 118 tilting but also are capable of independently performing a linear movement to secure a wide area for an operation, that is, a wide area for surgery. The first joints 111 are provided in a pair and coupled to each other in parallel.

The second joints 115 are coupled to end portions of the first joint 111 via hinges 112. Accordingly, the second joints 115 are capable of tilting to the first joints 111 and changing a relative position to the first joints 111 by the driving force supplied from the driving unit 120.

Referring to FIG. 1, the second joints 115 are coupled to the respective first joints 111 of the pair to form an overall shape of a pair of forceps.

As illustrated in FIGS. 2 and 3, each of the second joints 115 may include a plurality of, for example two, joint members 115a and 115b, that is, a front joint member 115b and a rear joint member 115a, wherein the joint members 115a and 115b are coupled by a hinge 116 so that the front joint member 115b may tilt to the rear joint member 115a.

The third joints 118 are coupled to end portions of the second joints 115 via hinges 119, and a tilting direction of the third joints 118 and a tilting direction of the second joints 115 may cross, for example, be perpendicular to each other.

Accordingly, the second joints 115 are capable of tilting to the first joints 111 in one direction, and the third joints 118 are capable of tilting to the second joints 115 in another direction, that is, in a direction perpendicular to the one direction, thereby precisely adjusting a position of the surgery unit 130 coupled to the position change unit 110.

The driving transmission section 121 may be disposed along one surface of the first joints 111 and the second joints 115 for relative movements of the second joints 115 to the first joints 111.

As mentioned above, the driving transmission section 121 of the present embodiment may be provided in a form of a plate spring type capable of generating sufficient torque, instead of a wire type.

The driving transmission section 121, as illustrated in FIG. 2, is disposed to be movable along an internal surface of the first joints 111 and an internal surface of the second joints 115, and an end portion may be fixed to the front joint member 115b of the second joints 115.

Thus, when the driving force is generated by the driving section 125 of the driving unit 120 to pull the driving transmission section 121 in the plate spring type, force generated with the driving transmission section 121 relatively unfolded is transmitted to the second joints 115, as shown in FIG. 3, and accordingly the second joints 115 may be moved in an internal direction with respect to the first joints 111.

In addition, a guide member 117 through which the driving transmission section 121 passes to move is provided on the internal surface of the second joint 115. Accordingly, when the force is transmitted from the driving section 125 to the driving transmission section 121, the driving transmission section 121 may smoothly move through an internal space of the guide member 117 without deviation.

As such, an extent of the driving force transmitted from the driving section 125 to the driving transmission section 121 is adjusted to adjust degree of unfolding of the driving transmission section 121, and accordingly a surgeon may easily and accurately change the position of the position change unit 110.

As described above, the driving transmission section 121 of the plate spring type is employed in lieu of a wire, and thus torque may be accurately transmitted when the positions of the joints 111, 115 and 118 are changed, thereby improving accuracy of the position change and increasing an area for surgery.

The surgery unit 130 of the present embodiment may be coupled to the position change unit 110 to be changed in position depending on the position change of the position change unit 110.

As illustrated in FIG. 1, the surgery unit 130 may include a connection section 131 disposed in a forming direction of the position change unit 110 and the surgery section 135 coupled to an end portion of the connection section 131 in a tilting manner.

The connection section 131 of the present embodiment may have flexibility for a position to be changed depending on the position change of the position change unit 110, thereby adjusting a position of the surgery portion 135. The connection section 131 may be partly fixed to the joints 111, 115 and 118 of the position change unit 110.

To this end, the position change unit 110 may include, as illustrated in FIG. 1, a plurality of coupling rings 114a and 114b for detachably coupling the connection section 131 and fixing a position of the connection section 131 to the position change unit 110. The connection section 131 is coupled to pass through the coupling rings 114a and 114b, thereby fixing the surgery unit 130 to the position change unit 110.

The surgery section 135, which is a part directly performing surgery on a surgical site 101, may perform an operation of, for example, incising the surgical site 101, as schematically illustrated in FIG. 4. The surgery section 135 is capable of not only tilting at the same spot with respect to the connection section 131 but also linearly moving forward and backward to precisely adjust an incision angle or position of the surgery section 135 with respect to the surgical site 101. The surgery section 135 may be replaced during surgery. That is, the surgery unit 135 may be forceps, scissors, or the like, which may be replaced during surgery if necessary, thereby improving efficiency and accuracy of the surgery.

As described above, since the joints 111, 115 and 118 of the position change unit 110 have a tilting structure in connected areas depending on operations of the driving transmission section 121, the connection section 131 of the surgery unit 130 coupled to the joints 111, 115 and 118 may also be changed in position depending on position changes of the joints 111, 115 and 118. In addition, the surgery section 135 has a tilting structure at the same spot with respect to the connection section 131, so that the surgeon may accurately control the position of the surgery section 135 with respect to the surgical site 101.

The surgery robot 100 of the present embodiment may further include a suction unit 150 fixed to the position change unit 110 to be adjusted in position based on position changes of the joints 111, 115 and 118 and an image capture unit 160 also coupled to the position change unit 110 to capture a video of a surgical procedure of the surgical site 101 during surgery in order to enhance reliability of the surgery.

The suction unit 150 of the present embodiment suctions a liquid used for surgery or a removed part from the surgical site 101 using a suction force externally provided to enhance reliability of the surgery.

The image capture unit 160 of the present embodiment captures a video of the surgical site 101 in real time so that the surgeon accurately identifies the position of the surgery section 135 with respect to the surgical site 101, and accordingly the surgeon may accurately perform the surgery while monitoring a screen captured by the image capture unit 160.

As described above, according to the embodiment of the present invention, the positions of the joints 111, 115 and 118 of the position change unit 110 for adjusting the position of the surgery unit 130 are adjusted not by a wire but by the driving transmission section 121 of the plate spring type which is capable of providing high torque, thereby ensuring sufficient force for surgery and securing a wide area for surgery.

In addition, accurate driving transmission is achieved by the driving transmission section 121 of the plate spring type to improve accuracy of a surgical procedure, and equipment may be installed at reduced cost, so that a high cost may not be imposed on patients, thus lightening a burden on the patients.

Although each of the second joints 115 includes the two joint members 115a and 115b, which are operated by the driving transmission section 121 of the plate spring type in the embodiment mentioned above, the two joint members 115a and 115b may also be operated separately. That is, one end of the driving transmission section 121 of the foregoing embodiment may be fixed to the front joint member 115b to adjust an angle of the front joint member 115b with respect to the rear joint member 115a by the driving force from the driving transmission section 121 (by a linear movement of the driving transmission section 121), or a separate driving transmission section (not shown) is installed for the first joints 111 and the rear joint member 115a to precisely adjust an angle of the rear joint member 115a to the first joints 111. Here, one end of the separate driving transmission section connecting the first joints 111 and the rear joint member 115a may be fixed to the rear joint member 115a, and a body portion thereof connected to the one end may be mounted to be movable in the lengthwise direction of the first joints 111 so that the rear joint member 115a may tilt to the first joints 111 by a linear movement of the separate driving transmission section.

Hereinafter, a surgery robot according to another embodiment of the present invention will be described, in which repeated descriptions of substantially the same components as those of the surgery robot according to the aforementioned embodiment will be omitted.

Figure 5:
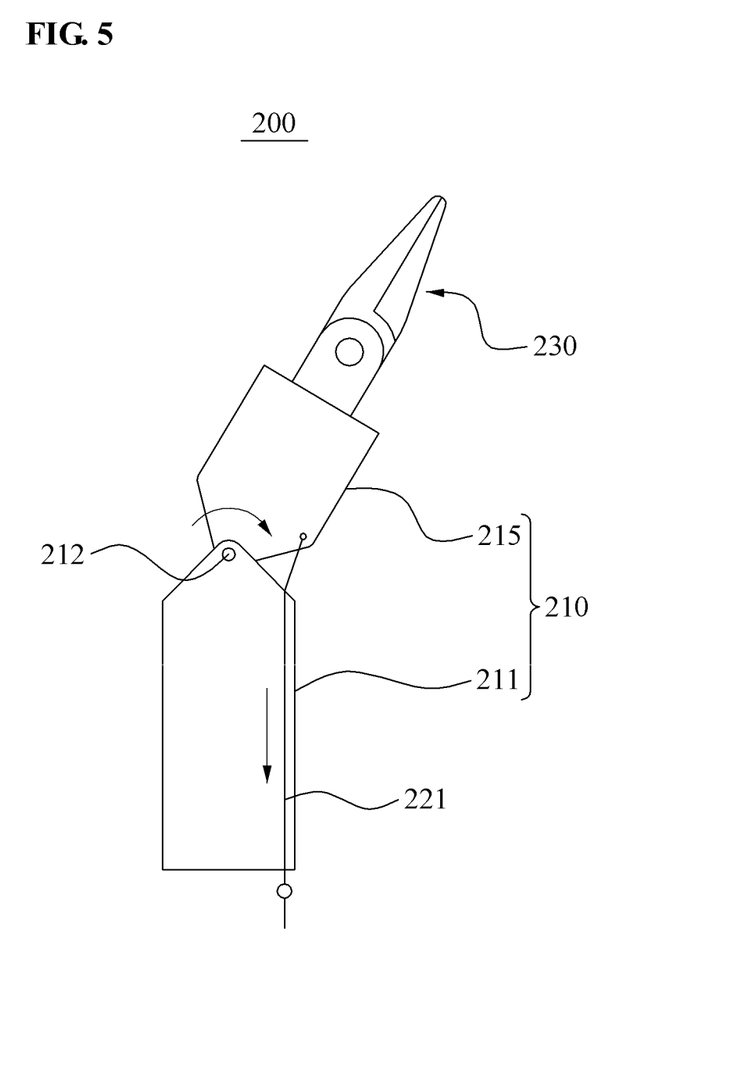
FIG. 5 schematically illustrates a surgery robot according to another embodiment of the present invention.

FIG. 5 illustrates a schematic configuration of the surgery robot according to the other embodiment of the present invention.

As illustrated, the surgery robot 200 according to the other embodiment of the present invention may include a surgery unit 210 which is introduced into a body and includes a plurality of joints 211 and 215 to change a position and a surgery section 230 at a front end portion thereof, a driving unit (not shown) to generate a driving force for changing a position of the surgery unit 210, and a driving transmission unit 221 disposed along the plurality of joints 211 and 215 and unfolded or bent by the driving force from the driving unit to change the position of the surgery unit 210.

In the present embodiment, the joints 211 and 215 of the surgery unit 210 are adjusted by the driving transmission unit 221 operated by the driving force from the driving unit, and the surgery section 230 is provided at the front end portion to perform surgery. That is, structural simplification may be achieved.

In the present embodiment, the driving transmission unit 221 of a plate spring type is disposed at one side of a first joint 211 and one side of a second joint 215 which are coupled to mutually rotate by a hinge 212, wherein one end thereof is fixed to the second joint 215. Thus, when the driving transmission unit 221 is pulled inward, the second joint 215 may rotate around the hinge 212. Conversely, when the driving is removed, the second joint 215 may return to an original state.

As described above, according to the other embodiment, positions of the joints 211 and 215 of the surgery unit 210 are adjusted not by a wire but by the driving transmission unit 221 of the plate spring type which is capable of providing high torque, thereby ensuring sufficient force for surgery, and structural simplification results in cost reduction. The present invention is not limited to the aforementioned embodiments, and it will be apparent to those skilled in the art that various modifications and variations can be made without departing from the idea and scope of the present invention. Thus, such modifications and variations are construed as being within the appended claims.

The invention claimed is:

1. A surgery robot comprising:
 a position change unit comprising at least one portion configured to be introduced into a body and comprising a plurality of joints to change a position;
 a surgery unit, coupled to the position change unit of which a position is to be changed along with a position change of the position change unit, comprising a surgery section for performing surgery on an affected area mounted on a front end portion thereof; and
 a driving unit configured to provide a driving force for the position change of the position change unit, wherein the driving unit comprises:
 (i) a driving section configured to generate the driving force, and
 (ii) a driving transmission section which is in the form of a plate spring and is disposed along one outer surface of the plurality of joints of the position change unit, wherein the driving transmission section is configured to receive the driving force and control a position of one joint with respect to another joint depending on a degree of unfolding or bending of the plate spring.

2. The surgery robot of claim 1, wherein the plurality of joints of the position change unit comprises a first joint in a lengthwise direction, a second joint coupled to the first joint in a tilting manner, and a third joint coupled to the second joint in a tilting manner, the third joint tilting in a direction crossing a direction of the second joint with respect to the first joint, and the driving transmission section is disposed along one surface of the first joint and one surface of the second joint and one end portion is fixed to the second joint.

3. The surgery robot of claim 1, further comprising a guide member provided on one surface of at least one of the joints, the guide member being configured to direct a movement of the driving transmission section.

4. The surgery robot of claim 1, wherein the surgery unit further comprises a connection section having flexibility to be partly fixed to the position change unit and coupled to the surgery section at an end portion thereof, and the surgery section is capable of tilting at the same spot with respect to the connection section.

5. The surgery robot of claim 4, wherein the position change unit comprises at least one coupling ring in a ring shape to which the connection section is coupled by passing therethrough to detachably couple the surgery unit to the position change unit.

6. The surgery robot of claim 1, further comprising a suction unit coupled to the position change unit to remove a material generated at a surgical site during surgery by the surgery unit.

7. The surgery robot of claim 1, further comprising an image capture unit coupled to the position change unit to capture a video of a surgical procedure or position of the surgery section in real time during surgery by the surgery unit.

8. The surgery robot of claim 1, which is configured to adjust the positions of the joints without using a wire between the joints.

9. A surgery robot comprising:
 a surgery unit having at least one portion configured to be introduced into a body and comprising a plurality of joints to change a position and a surgery section at a front end portion thereof;
 a driving unit comprising a driving section configured to generate a driving force for changing a position of the surgery unit; and
 a driving transmission unit disposed along an outer surface of the plurality of joints and configured to be unfolded or bent by the driving force from the driving unit to change the position of the surgery unit, wherein the driving transmission section is provided in a form of a plate spring type and wherein the driving transmission section is configured to change positions of the joints depending on a degree of unfolding or bending of the plate spring.

10. The surgery robot of claim 9, wherein the plurality of joints comprises a first joint; and a second joint coupled to the first joint in a hinged manner, and the driving transmission unit is disposed along one side of the first joint and one side of the second joint and one end is fixed to the second joint.

11. The surgery robot of claim 9, which is configured to adjust the positions of the joints without using a wire between the joints.

* * * * *